(12) United States Patent
Farghaly et al.

(10) Patent No.: US 7,964,736 B2
(45) Date of Patent: Jun. 21, 2011

(54) PHOSPHAGEN SYNTHESIS

(75) Inventors: Ahmed Farghaly, Alexandria (EG); Elgebaly A. Salwa, Edgewater, MD (US)

(73) Assignee: Nour Heart, Inc., Edgewater, MD (US)

( * ) Notice: Subject to any disclaimer, the term of this patent is extended or adjusted under 35 U.S.C. 154(b) by 595 days.

(21) Appl. No.: 11/794,589

(22) PCT Filed: Dec. 29, 2005

(86) PCT No.: PCT/US2005/047019
§ 371 (c)(1),
(2), (4) Date: Dec. 7, 2007

(87) PCT Pub. No.: WO2006/073923
PCT Pub. Date: Jul. 13, 2006

(65) Prior Publication Data
US 2008/0242639 A1 Oct. 2, 2008

Related U.S. Application Data

(60) Provisional application No. 60/640,061, filed on Dec. 30, 2004.

(51) Int. Cl.
*C07F 9/6506* (2006.01)
*C07D 233/46* (2006.01)
(52) U.S. Cl. .................. 548/111; 548/331.5; 548/332.5
(58) Field of Classification Search .................. 548/111, 548/331.5, 332.5
See application file for complete search history.

(56) References Cited

OTHER PUBLICATIONS

Annesley et al. The Journal of Biological Chemistry 1980, 255(9), 3924-30.*
Struve et al. J. Org. Chem. 1977, 42(25), 4035-4040.*
Jones et al. J. Chem. Soc. 1949, 547-552.*

* cited by examiner

*Primary Examiner* — Jason M Nolan
(74) *Attorney, Agent, or Firm* — Greenblum & Bernstein, PLC

(57) ABSTRACT

Cyclocreatine phosphate can be prepared in large quantities from inexpensive starting materials to afford a stable product.

6 Claims, No Drawings

PHOSPHAGEN SYNTHESIS

CLAIM OF PRIORITY

This application is the National Stage application of PCT application number PCT/US2005/047019, filed Dec. 29, 2005, which claims priority to U.S. patent application Ser. No. 60/640,061, filed Dec. 30, 2004, both of which is are incorporated by reference in its entirety their entireties.

TECHNICAL FIELD

This invention relates to synthesis of a phosphagen.

BACKGROUND

Dietary ingestion of the creatine analogue cyclocreatine (1-carboxymethyl-2-iminoimidazolidine, CCr) imparts to tissue the ability to sustain high levels of myocardial adenosine triphosphate (ATP), or at least to delay the depletion of ATP during total ischemia. Cyclocreatine is reported to be effective provided the dietary supplement is ingested over a period of at least two days prior to the onset of ischemia; but a maximum response is achieved where the dietary supplement has been provided over a period of about ten to fourteen days prior to onset of ischemia. This period of time can be required in order to permit the dietary supplement, cyclocreatine, to undergo phosphorylation (to form cyclocreatine phosphate, 1-carboxymethyl-2-imino-3-phosphono-imidazolidine, CCrP). This synthetic phosphagen is believed to be effective in helping to conserve the total adenylate pool and to buffer the decrease in the ratio of ATP to free adenosine diphosphate (ADP) that results from ischemia. Dietary ingestion of cyclocreatine also delays the development of acidosis and the onset of poor ventricular compliance, as evidenced by a rigor-like increase in tonic pressure, during ischemia.

SUMMARY

The creatine analogs cyclocreatine (CCr) and cyclocreatine phosphate (CCrP), when administered prior to ischemia, delay ATP depletion during ischemia and can restore cardiac function in models of hypothermic cardioplegic cardiac arrest (e.g., models of bypass surgery), regional warm ischemia (e.g., models of acute myocardial infarction), and global warm ischemia (e.g., models of cardiac arrest). Advantageously, CCrP can have beneficial effects when administered after ischemia occurs. CCrP can be synthesized from inexpensive starting materials in a stable form. The synthesis can be performed on a large scale, such as more than 100 grams, more than 1 kilogram, or 10 kilograms or more.

In one aspect, a method of making a compound having the formula:

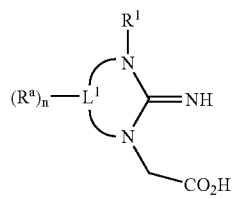

where $L^1$ is $C_1$-$C_4$ alkylene; $R^1$ is —H or —P(=O)(OH)$_2$; each $R^a$, independently, is hydrogen, alkyl, alkoxy, aryl, aralkyl, hydroxy, or halo; and n is 0, 1, 2, 3 or 4; or a pharmaceutically acceptable salt thereof, includes contacting a compound having the formula:

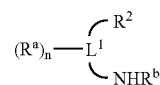

where $L^1$ is $C_1$-$C_4$ alkylene; each $R^a$, independently, is hydrogen, alkyl, alkoxy, aryl, aralkyl, hydroxy, or halo; $R^2$ is hydroxy, alkoxy, or aryloxy; $R^b$ is hydrogen or alkyl; and n is 0, 1, 2, 3 or 4; with a compound having the formula $L^2$-$CH_2$—CN, wherein $L^2$ is a leaving group.

A compound having the formula:

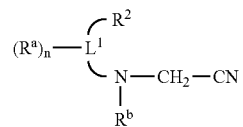

can be converted into a compound having the formula:

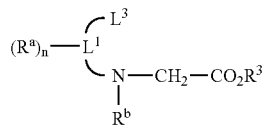

where $L^1$ is $C_1$-$C_4$ alkylene; each $R^a$, independently, is hydrogen, alkyl, alkoxy, aryl, aralkyl, hydroxy, or halo; $R^b$ is hydrogen or alkyl; $L^3$ is a leaving group; and $R^3$ is hydrogen, alkyl or aryl; and n is 0, 1, 2, 3 or 4.

A compound having the formula:

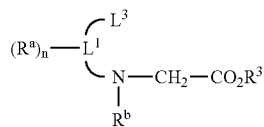

can be converted into a compound having the formula:

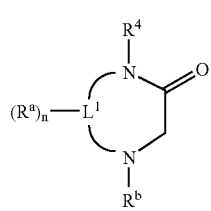

where $L^1$ is $C_1$-$C_4$ alkylene; each $R^a$, independently, is hydrogen, alkyl, alkoxy, aryl, aralkyl, hydroxy, or halo; $R^b$ is hydrogen or alkyl; $R^4$ is hydrogen, aralkyl or a protecting group; and n is 0, 1, 2, 3 or 4.

A compound having the formula:

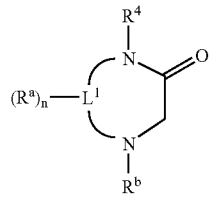

can be converted into a compound having the formula:

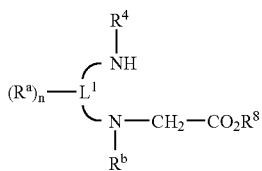

where $L^1$ is $C_1$-$C_4$ alkylene; each $R^a$, independently, is hydrogen, alkyl, alkoxy, aryl, aralkyl, hydroxy, or halo; $R^b$ is hydrogen or alkyl; $R^4$ is hydrogen, aralkyl or a protecting group; $R^8$ is hydrogen, alkyl, aryl, or a cation; and n is 0, 1, 2, 3 or 4.

A compound having the formula:

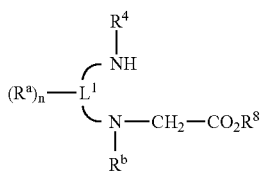

can be converted into a compound having the formula:

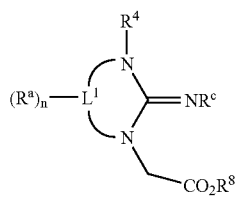

where $L^1$ is $C_1$-$C_4$ alkylene; each $R^a$, independently, is hydrogen, alkyl, alkoxy, aryl, aralkyl, hydroxy, or halo; $R^4$ is hydrogen, aralkyl or a protecting group; $R^8$ is hydrogen, alkyl, aryl, or a cation; $R^c$ is hydrogen, alkyl, aralkyl, or a protecting group; and n is 0, 1, 2, 3 or 4.

A compound having the formula:

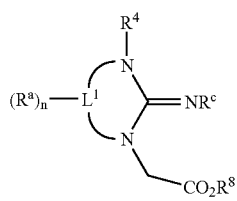

can be converted into a compound having the formula:

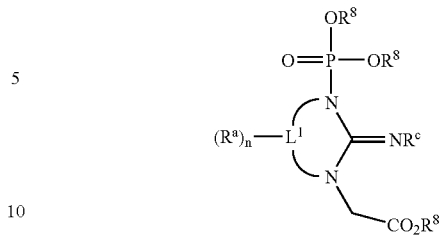

where $L^1$ is $C_1$-$C_4$ alkylene; each $R^a$, independently, is hydrogen, alkyl, alkoxy, aryl, aralkyl, hydroxy, or halo; $R^4$ is hydrogen, aralkyl or a protecting group; each $R^8$, independently, is hydrogen, alkyl, aryl, or a cation; $R^c$ is hydrogen, alkyl, aralkyl, or a protecting group; and n is 0, 1, 2, 3 or 4; or a pharmaceutically acceptable salt thereof.

A compound having the formula:

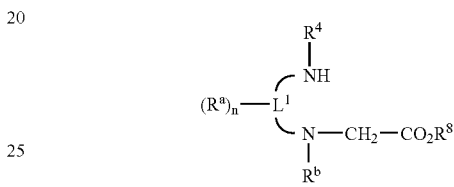

can be converted into a compound having the formula:

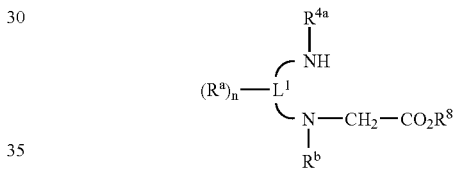

where $L^1$ is $C_1$-$C_4$ alkylene; each $R^a$, independently, is hydrogen, alkyl, alkoxy, aryl, aralkyl, hydroxy, or halo; $R^b$ is hydrogen or alkyl; $R^{4a}$ is hydrogen or —P(=O)(OH)$_2$; $R^8$ is hydrogen, alkyl, aryl, or a cation; and n is 0, 1, 2, 3 or 4; or a pharmaceutically acceptable salt thereof.

A compound having the formula:

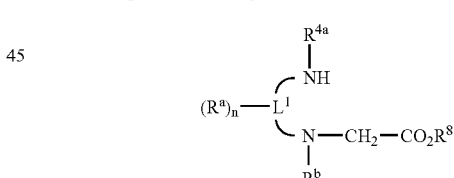

can be converted into a compound having the formula:

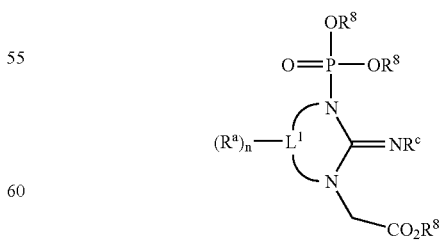

where $L^1$ is $C_1$-$C_4$ alkylene; each $R^a$, independently, is hydrogen, alkyl, alkoxy, aryl, aralkyl, hydroxy, or halo; $R^b$ is hydrogen or alkyl; $R^4$ is hydrogen, aralkyl or a protecting group; each $R^8$, independently, is hydrogen, alkyl, aryl, or a cation;

$R^c$ is hydrogen, alkyl, aralkyl, or a protecting group; and n is 0, 1, 2, 3 or 4; or a pharmaceutically acceptable salt thereof.

In some circumstances, $L^1$ can be $C_2$ alkylene, each $R^a$ can be hydrogen, and $R^c$ can be hydrogen.

In another aspect, a method of making a compound having the formula:

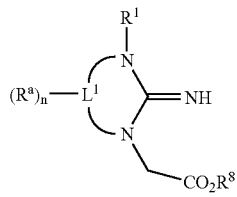

where $L^1$ is $C_1$-$C_4$ alkylene; $R^1$ is —H or —P(=O)(OH)$_2$; each $R^a$, independently, is hydrogen, alkyl, alkoxy, aryl, aralkyl, hydroxy, or halo; $R^8$ is hydrogen, alkyl, aryl, or a cation; and n is 0, 1, 2, 3 or 4; or a pharmaceutically acceptable salt thereof; includes forming a compound having the formula:

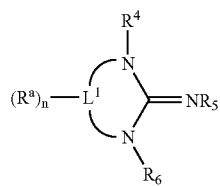

where $L^1$ is $C_1$-$C_4$ alkylene; each $R^a$, independently, is hydrogen, alkyl, alkoxy, aryl, aralkyl, hydroxy, or halo; and n is 0, 1, 2, 3 or 4; $R^4$ is hydrogen, aralkyl or a protecting group, $R^5$ is a protecting group; and $R^6$ is hydrogen, a protecting group, or has the formula —CH$_2$CO$_2$R$^8$, wherein $R^8$ is hydrogen, alkyl, aryl, or a cation.

Forming the compound having the formula:

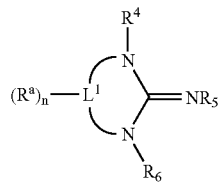

can include protecting an imino nitrogen of 2-iminoimidazolidine.

A compound having the formula:

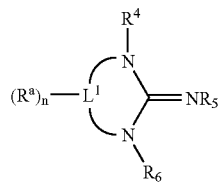

can be converted into a compound having the formula:

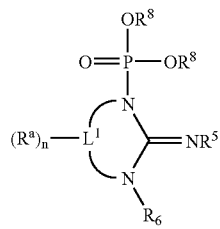

where $L^1$ is $C_1$-$C_4$ alkylene; each $R^a$, independently, is hydrogen, alkyl, alkoxy, aryl, aralkyl, hydroxy, or halo; n is 0, 1, 2, 3 or 4; $R^5$ is a protecting group; $R^6$ is hydrogen, a protecting group, or has the formula —CH$_2$CO$_2$R$^8$; and each $R^8$, independently, is hydrogen, alkyl, aryl, or a cation.

A compound having the formula:

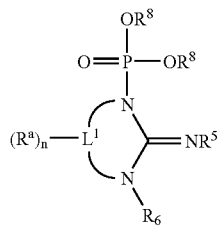

can be converted into a compound having the formula:

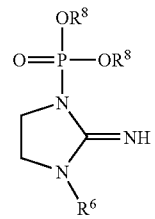

where $R^6$ is hydrogen, a protecting group, or has the formula —CH$_2$CO$_2$R$^8$; and each $R^8$, independently is hydrogen, alkyl, aryl, or a cation.

A compound having the formula:

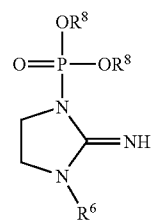

can be converted into a compound having the formula:

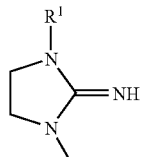

where $R^1$ is —H or —P(=O)(OH)$_2$, or a pharmaceutically acceptable salt thereof.

In another aspect, an ischemic condition in animal tissue can be treated by administering to a subject a compound having the formula:

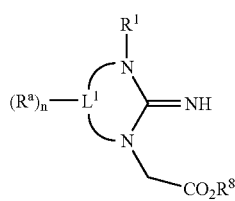

wherein $L^1$ is $C_1$-$C_4$ alkylene; $R^1$ is —H or —P(=O)(OH)$_2$; each $R^a$, independently, is hydrogen, alkyl, alkoxy, aryl, aralkyl, hydroxy, or halo; $R^8$ is hydrogen, alkyl, aryl, or a cation; and n is 0, 1, 2, 3 or 4; or a pharmaceutically acceptable salt thereof. The tissue can include muscle tissue. The muscle tissue can include cardiac muscle tissue.

The details of one or more embodiments are set forth in description below. Other features, objects, and advantages will be apparent from the description and from the claims.

DETAILED DESCRIPTION

Young chicks and rats fed CCr for 10 to 19 days accumulated massive amounts of cyclocreatine phosphate (CCrP), demonstrating phosphorylation and intracellular storage of CCr as CCrP. See, for example, Roberts, J. J. and Walker, J. B., *Am. J. Physiol.* 243: H911-H916, 1982; and Roberts, J. J. and Walker, J. B., *Arch. Biochem. Biophys.* 200: 563-571, 1983, each of which is incorporated by reference in its entirety.

Myocardial ATP levels were sustained substantially longer during ischemia compared to control hearts. Because CCrP is a long-acting phosphagen, it helps to sustain ATP levels longer during ischemia compared to controls containing creatine phosphate (CrP) as the sole phosphagen. Studies showed that CCrP possesses a substantially less negative Gibbs standard free energy of hydrolysis than CrP and, therefore, it continues to buffer thermodynamically the adenylate system at the lower pH values and lower cytosolic phosphorylation potentials that occur during the latter stages of ischemia, conditions in which CrP is no longer effective (see, for example, Griffiths, G. R. and Walker J. B., *J. Biol. Chem.* 251: 2049-2054, 1976, which is incorporated by reference in its entirety).

Furthermore, because the heart relies almost exclusively on mitochondrial oxidative phosphorylation for high-energy phosphate production, a decrease in oxygen delivery below a critical limit-due to pathological block of adequate blood supply, asphyxia, poisoning, or experimental and surgical intervention, will change cardiac energy metabolism. Research showed that contractile performance in-vivo decreases precipitously and ceases when 75% of CrP is depleted, but only when 20% of ATP. See, for example, Gudbjamason S, et al., *J. Mol. Cell. Cardiol.* 1:325-339, 1970, which is incorporated by reference in its entirety.

Isolated ischemic rabbit hearts treated with CCr maintained high levels of ATP and CrP, whereas control hearts treated with saline or creatine (Cr), which lost more than 95% of ATP and CrP (see, for example, Elgebaly S A, et al., *Am. J. Pathol.* 137:1233-1241, 1990, which is incorporated by reference in its entirety). Preservation of ATP would likely explain the significant reduction of Nourin-1 released by CCr treated hearts and the high release of Nourin-1 by controls (see Elgebaly S A, et al., *Surg. Forum* 41:274-278, 1991; and U.S. Pat. No. 5,091,404, each of which is incorporated by reference in its entirety). In the intact canine model of coronary artery occlusion followed by reperfusion, CCr-treated hearts maintained 85% of the ATP (loss of 15%) and 97% of the CrP (loss of 3%) of normal non-ischemic levels (see Elgebaly S A, et al. *J. Pharmacol. Exp. Therap.* 266(3): 1670-1677, 1993, which is incorporated by reference in its entirety). Control saline treated hearts, on the other hand, maintained 66% of the ATP (loss of 34%) and 18% of the CrP (loss of 83%). A number of studies have also established that the decline in ATP associated with ischemia could have many adverse consequences, including loss of ionic gradients, resulting in a calcium overload and activation of endogenous phospholipases or proteases. Catabolites of lipid degradation may act as a detergent and damage cell membranes, leading to edema. Adenosine nucleotides and bases accumulate and might be a major source of free radicals via the xanthine oxidase reaction (see Reimer, K. A., et al, *J. Mol. Cell. Cardiol.* 21: 1255-1239, 1989, which is incorporated by reference in its entirety).

CCr is effective when administered prior to the induction of ischemia. Long-term feeding of rats and chickens (up to 3 weeks) with 1% CCr significantly delayed the reduction of myocardial ATP, exhaustion of high-energy phosphates, and onset of rigor tension during cardiac ischemia. Upon reperfusion, the number of hearts recovering mechanical function was significantly higher in CCr treated rats compared to controls (see Roberts, J. J. and Walker, J. B., *Am. J. Physiol.* 243: H911-H916, 1982, which is incorporated by reference in its entirety).

Short-term administration (30-120 min) of CCr is as effective in protecting the heart from ischemic injury as long-term administration for up to 21 days. Intravenous injection in dogs, rabbits, and rats of CCr 30-120 min prior to the induction of ischemia reduced the cardiac production of Nourin-1 and the accumulation of neutrophils into the myocardium during reperfusion (see, for example, Elgebaly S A, et al., *Am. J. Pathol.* 137:1233-1241, 1990; and Elgebaly S A, et al, *J. Pharmacol. Exp. Therap.* 266(3):1670-1677, 1993, each of which is incorporated by reference in its entirety). In a limited study, however, when isolated rabbit hearts were perfused with CCr, without preinjection with the drug, no protection was observed (i.e., elevated levels of Nourin-1 and low levels of ATP and CrP). Although, it appears from this limited study that the administration of CCr prior to ischemia is necessary for myocardial protection and release of Nourin-1, studies by Walker's group demonstrated that incubating chopped whole brain with 0.5% CCr in-vitro for 90 minutes protected brain tissues from ischemic injury (see, for example, Wozincki D. T., Walker J. B., *J. Neurochemistry,* 50, 1640-1647, 1988, which is incorporated by reference in its entirety).

CCr and CCrP promoted significant restoration of cardiac function and preservation of ATP and CrP. In intact canine models of myocardial ischemia followed by reperfusion, as well as isolated rat heart working models, drug administration prior to ischemia protected the hearts against warm and hypothermic ischemia, in the presence and absence of cardioplegic arrest, and when ischemia was induced for 40 min, 2.5 hours, and 6 hours. See, for example, Allam M E, et al., *Surg. Forum*

XLI:246-249, 1990; Elgebaly S A, et al., *Transplantation* 57(1) 1-6, 1994; and Houser S L, et al., *J. Mol. Cell. Cardiol.* 27:1065-1073, 1995, each of which is incorporated by reference in its entirety. Table 1 summarizes these studies.

TABLE 1

| Ischemia | time | animal | drug | results |
|---|---|---|---|---|
| Regional warm ischemia (LAD) (intact AMI model) | 1 hr | canine | CCr | Restoration |
| Global warm ischemia (intact cardiac arrest model) | 7, 9, 10 min | rat | CCr | Restoration |
| Hypothermic cardioplegic arrest (intact bypass surgery model) | 1 hr | canine | CCr | Restoration |
| Hypothermic cardioplegic arrest (intact bypass surgery model) | 3 hrs | canine | CCr | Restoration |
| Normothermic cardioplegic arrest | 40 min | rat | CCr | Restoration |
| Normothermic cardioplegic arrest | 40 min | rat | CCrP | Restoration |
| Hypothermic cardioplegic arrest | 2.5 hrs | rat | CCrP | Restoration |
| Hypothermic cardioplegic arrest | 6 hrs | rat | CCrP | Restoration |

Thus, administration of CCr and CCrP protects myocardial tissues and restore cardiac function in models of acute myocardial infarction, global cardiac arrest, coronary bypass surgery, and heart transplant.

In the heart transplant rat model, CCrP did not only improve the recovery of function during reperfusion after 6 hours of cold storage, but also significantly reduced the increase in heart weight compared to control untreated hearts. Furthermore, although CCrP treatment improved functional recovery and reduced tissue edema, there was no detectable difference between the treated and control groups in regard to myocardial cell injury, as measured by electron microscopy. Both groups showed mild ischemic changes and no significant ultrastructural differences. Similarly, no significant leakage of creatine kinase (CK) was detected during reperfusion from control and CCrP-treated groups (see Elgebaly S A, et al., *Transplantation* 57(1) 1-6, 1994, which is incorporated by reference in its entirety).

Prior feeding of CCr to rats delayed ATP depletion and the onset of rigor in ischemic isolated hearts (see Roberts, J. J. and Walker, J. B.: Feeding a creatine analogue delays ATP depletion and onset of rigor in ischemic heart. *Am. J. Physiol.* 243: H911-H916, 1982, which is incorporated by reference in its entirety). The reduction of ischemic contracture (rigor) was associated with delayed development of acidosis. Furthermore, the hearts of CCr-fed rats spontaneously defibrillated sooner during reperfusion than did the hearts in control rats. In a bypass surgery model, canines treated with CCr defibrillated spontaneously, whereas untreated canines required external defibrillation.

As described above, although the mechanism by which CCr preserves the heart during ischemia and restores cardiac function during reperfusion is not fully understood, it is likely to be related to preservation of ATP. CCr has no inotropic or chronotropic effect on dog hearts. Since the breakdown of ATP is the immediate source of energy for contraction, and that contractile performance decreases precipitously and ceases when only 20% of ATP is depleted, the reported CCr preservation of over 85% of ATP (loss of only 15%) in ischemic myocardium is likely the major contributor to the observed restoration of post-ischemic myocardial contractility (see Allam M E, et al., *Surg. Forum* XLI:246-249, 1990, which is incorporated by reference in its entirety).

Extensive work on myocardial preservation by CrP was published between 1980-1995, primarily by Saks V A in Russia and Hearse D in the United Kingdom. Even though intravenous administration of CrP increased intracellular ATP & CrP, and decreased CK release in the hearts of living rats, CrP is generally accepted not to be membrane permeable. The cardioprotection by CrP is believed to be brought about by extracellular effects (see, for example, Down W. H., Chasseaud L. F., and Ballard, S. A.: The effect of intravenous administration of phosphocreatine on ATP and phosphocreatine concentrations in the cardiac muscle of the rat. Arzneim-Forsch/Drug Res 33: 552-4, 1983; and Korge P, Silber M L: Effect of creatine phosphate on the contractile activity in acutely failing rat heat. Cardioplegia 43: 1345-1354, 1998, each of which is incorporated by reference in its entirety). Research further indicated that CrP has an important membrane-stabilizing effect by interacting electrostatically with membrane phopholipids, thus decreasing the fluidity and possibly increasing the stability of the plasma membrane.

As described below (Table 2), intravenous injection of rats with CrP, and CCrP prior to subjecting the hearts in-vitro to normothermic arrest for 40 min at 37° C. significantly improved the recovery of cardiac function compared to control saline-treated hearts. Furthermore, when CrP was placed in the perfusate solution directly without pre-injecting the rats with CrP, hearts continued to show significant improvement of cardiac function. These results suggest that CCrP administration post-ischemia will also likely exert cardiac protection against ischemic injury.

Although CCrP, and CrP improved post-ischemic cardiac function when hearts were subjected to normothermic arrest for 40 min at 37° C., only CCrP continued to exert cardioprotection when rat hearts were exposed to hypothermic arrest for 2.5 hours at 22° C. and 6 hours at 4° C. CrP failed to exert any cardioprotection under hypothermic conditions (2.5 hours at 22° C.) when CrP was injected in-vivo prior to isolating the hearts or placed directly in the perfusate solutions. Results of this study demonstrate the superiority of CCrP over CrP in protecting the hearts against normothermic and hypothermic ischemia.

TABLE 2

| Ischemia | time | animal | drug | results |
|---|---|---|---|---|
| drug injected intravenously prior to ischemia | | | | |
| Normothermic cardioplegic arrest | 40 min | rat | CCrP | Restoration |
| Hypothermic cardioplegic arrest | 2.5 hrs | rat | CCrP | Restoration |
| Hypothermic cardioplegic arrest | 6 hrs | rat | CCrP | Restoration |
| Normothermic cardioplegic arrest | 40 min | rat | CrP | Restoration |
| Hypothermic cardioplegic arrest | 2.5 hrs | rat | CrP | No Restoration |
| drug perfused after removal of the heart (post-ischemia) | | | | |
| Normothermic cardioplegic arrest | 40 min | rat | CrP | Restoration |
| Hypothermic cardioplegic arrest | 2.5 hrs | rat | CrP | No Restoration |

In a dose-response study, CCr exerted a strong cardioprotective effect at 600 mg/kg and 300 mg/kg. No effect was observed, however, at 150 mg/kg. CCrP also exerted strong cardioprotective effect at 1000 mg/kg, 667 mg/kg, and 484 mg/kg, but not at 300 mg/kg. In a molar equivalent basis, CrP was effective at 510 mg/kg when injected intravenously and at 10 mM when placed in the perfusate.

Using isolated rabbit hearts, intravenous administration of CCr (600 mg/kg) for 2 hours prior to removing and perfusing hearts in-vitro for additional two hours did not induce tissue damage. After 2 hours reperfusion, control hearts showed patches of eosinophilic degeneration of myocardial fiber cytoplasm characteristic of early ischemia in myocardium. Patches of contraction bands associated with ischemia were also evident. CCr-treated hearts, on the other hand, showed only occasional small foci of contraction bands and no significant eosinophilic changes. Similar results were obtained when we used the intact canine model of coronary occlusion followed by reperfusion (LAD for 1 hour, and 2 hours reperfusion). The administration of CCr showed marked reduction in cell damage compared to control hearts. As described above, the reduction in myocardial cell injury in CCr-treated hearts was associated with significant restoration of cardiac function further confirming that CCr is not toxic to heart tissues.

Cyclocreatine phosphate can be administered as a pharmaceutically acceptable salt. A pharmaceutically acceptable salt refers to a salt prepared from pharmaceutically acceptable non-toxic bases or acids including inorganic or organic bases and inorganic or organic acids. Salts derived from inorganic bases include salts with one or more of the following cations: aluminum, ammonium, calcium, copper, ferric, ferrous, lithium, magnesium, manganic, manganous, potassium, sodium, zinc, and the like. Particularly preferred are ammonium, calcium, magnesium, potassium and sodium salts.

Salts derived from pharmaceutically acceptable organic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropyulamine, lysine, methylglucamine, morpholine, piperazine, piperidine, polyamine resins, procaine, purines, theobromine, triethylamine, trimethylamine, tripropylamine, tromethamine, and the like.

When the compound is basic, salts may be prepared from pharmaceutically acceptable acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, oxalic, succinic, sulfuric, tartaric, p-toluenesulfonic acid, and the like. Particularly preferred are benzenesulfonic, citric, hydrobromic, hydrochloric, maleic, phosphoric, oxalic, sulfuric and tartaric acids.

It can be desirable to protect a functional group during preparation of CCr or CCrP. For example, an amino group can be protecting with a protecting group to prevent undesired reactions of the amino group. A protecting group is a suitable chemical group which may be attached to a functional group of a molecule, then removed at a later stage to reveal the intact functional group and molecule. Examples of suitable protecting groups for various functional groups are described in Theodora W. Greene, Peter G. M. Wuts: *Protective Groups in Organic Synthesis*, 3$^{rd}$ ed. Wiley Interscience, 1999; L. Fieser and M. Fieser, *Fieser and Fieser's Reagents for Organic Synthesis*, John Wiley and Sons (1994); L. Paquette, ed. *Encyclopedia of Reagents for Organic Synthesis*, John Wiley and Sons (1995); each of which is incorporated by reference in its entirety.

Cyclocreatine can be made according to the methods described in Griffiths, G. R., et al., *J. Biol. Chem.* 251, 2049-2054, 1976, which is incorporated by reference in its entirety. Briefly, ethylenediamine is allowed to react with sodium chloroacetate. The product is treated with NaOH and cyanogen bromide added. See Scheme 1.

Scheme 1

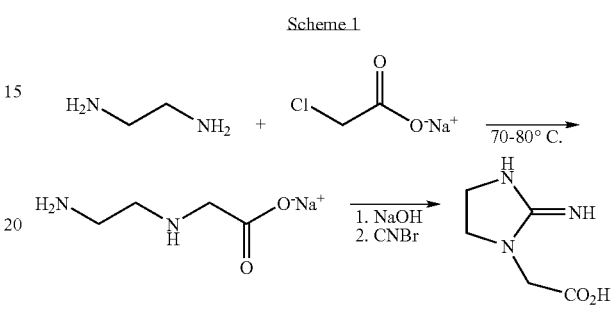

Cyclocreatine phosphate can be prepared by reacting cyclocreatine with phosphorus oxychloride under basic conditions (Scheme 2). See, for example, Annesley, T. M., et al., *Biochem. Biophys. Res. Commun.* 74, 185-190, 1977, which is incorporated by reference in its entirety.

Scheme 2

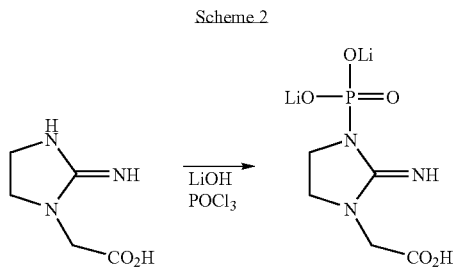

EXAMPLES

In general, cyclocreatine, cyclocreatine phosphate, and analogous compounds can be prepared according to Scheme 3.

Scheme 3

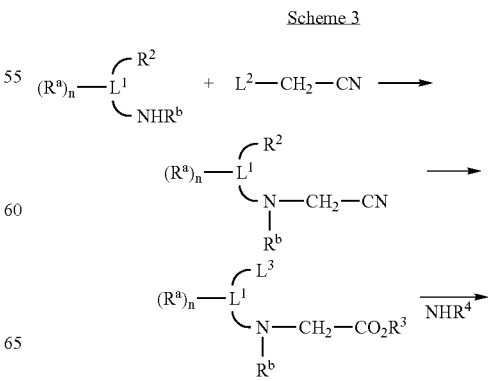

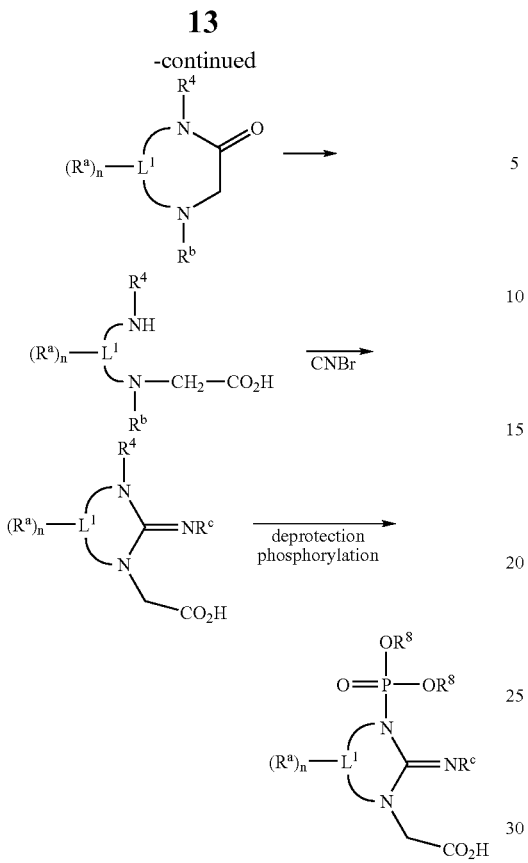

In Scheme 3, $L^1$ is $C_1$-$C_4$ alkylene and each $R^a$, independently, is hydrogen, alkyl, alkoxy, aryl, aralkyl, hydroxy, or halo; and n is 0, 1, 2, 3, or 4. $R^2$ is hydroxy, alkoxy, or aryloxy. $R^b$ is hydrogen or alkyl. $L^2$ and $L^3$ are each, independently, a leaving group. A leaving group is a functional group that can be displaced, for example, by a nucleophilic group. Examples of leaving groups include hydroxide, and halogens. Other examples of leaving groups can be found, for example, in Smith, M. B. and March, J., *March's Advanced Organic Chemistry: Reactions, Mechanisms, and Structure*, 5th Edition, Wiley-Interscience, 2001, which is incorporated by reference in its entirety. $R^3$ is hydrogen, alkyl or aryl. $R^4$ is hydrogen, aralkyl or a protecting group. $R^c$ is hydrogen, alkyl, aralkyl, or a protecting group. $R^8$ is hydrogen, alkyl, aryl, or a cation. The cation can be, for example, $H^+$, $L^+$, $Na^+$, $K^+$, $Mg^{2+}$, $Ca^{2+}$, or $NH_4^+$.

Cyclocreatine can be converted to a desired pharmaceutically acceptable salt by treatment with an appropriate acid. For example, cyclocreatine can be converted to its oxalate salt, benzenesulfonate (besylate) salt, or maleate salt.

A solution is prepared by dissolving 10 mmol of cyclocreatine in the minimum amount of distilled water. To this solution 20 mmol of oxalic acid (as a saturated ethanol solution) are added with stirring. Stirring is continued for five minutes, then the mixture is filtered and washed with ethanol and ether. The resulting cyclocreatine oxalate solid is dried in vacuo and has a melting point above 350° C. with decomposition.

A solution is prepared by dissolving 10 mmol of cyclocreatine in the minimum amount of distilled water. To this solution 20 mmol of benzenesulfonic acid (as a saturated methylene chloride solution) are added with stirring. Stirring is continued for ten minutes, then the mixture is filtered and washed with ethanol and ether. The resulting cyclocreatine benzenesulfonate solid is dried in vacuo and has a melting point above 350° C. with decomposition.

A solution is prepared by dissolving 10 mmol of cyclocreatine in the minimum amount of distilled water. To this solution 20 mmol of maleic acid (as a saturated ethanol solution) are added with stirring. Stirring is continued for five minutes, then the mixture is filtered and washed with ethanol and ether. The resulting cyclocreatine maleate solid is dried in vacuo and has a melting point above 350° C. with decomposition.

Cyclocreatine phosphate, and derivatives thereof, can be prepared by modifying Scheme 1 and Scheme 2. Alternatively, cyclocreatine phosphate can be prepared using ethanolamine and cyanohydrin (sometimes referred to as hydroxyacetonitrile or glycolonitrile) as starting materials. See Scheme 4.

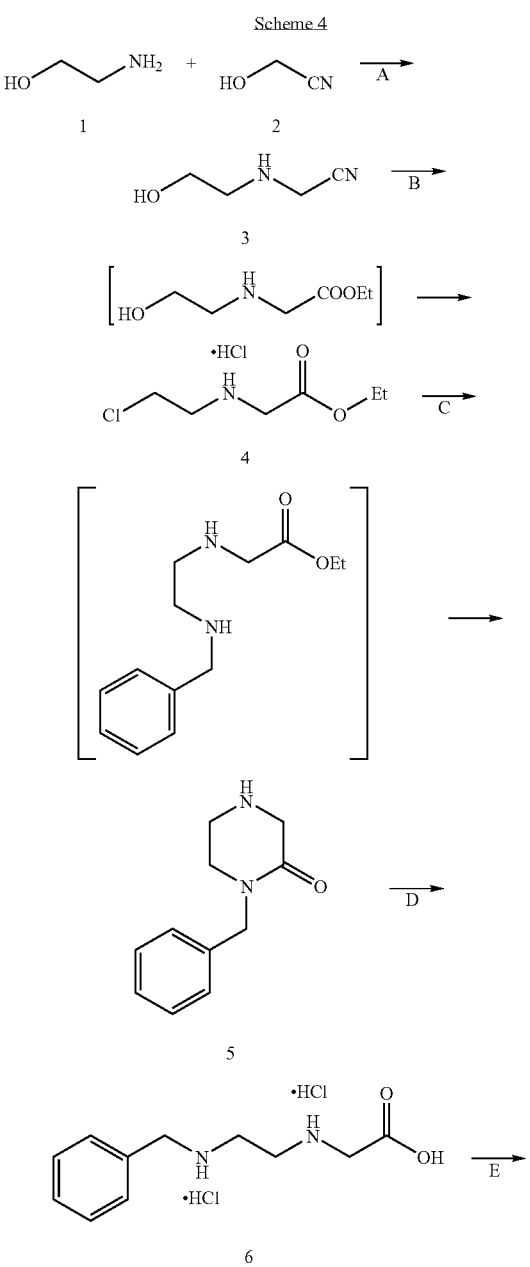

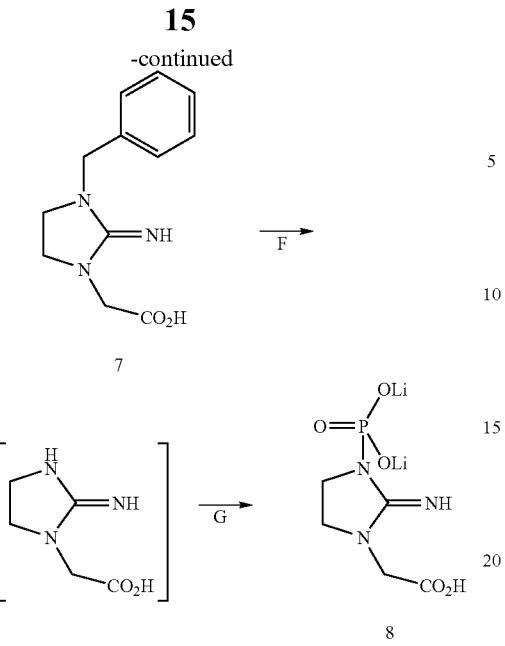

(A) Equimolar amounts of pre-cooled ethanolamine 1 and cyanohydrin 2 are mixed in a drop-wise manner with stirring. Stirring is continued overnight. The reaction mixture is evacuated to 5 mm Hg with stirring and cooling, whereupon a semi-solid mass, 2-hydroxyethylaminoacetonitrile 3, is obtained. This intermediate 3 is suitable for further reaction without further purification.

(B) A suitable amount of 3 is added very cautiously with cooling in an ice bath to a large volume of absolute ethanol saturated with HCl gas, with stirring. Stirring is continued for further 2 hours. The reaction is then heated under reflux for 2 hours, filtered, and evaporated to remove ethanol. The residue is dissolved in $CHCl_3$, cooled in ice, and added with stirring to a solution of thionyl chloride in $CHCl_3$ in a dropwise manner. Stirring is continued at room temperature for 2 hours. The solvent is evaporated. A large volume of ether is added, the crude product is collected, purified by washing with ether and characterized as ethyl-N-(2-chloroethyl)glycine HCl, 4.

(C) A solution of 4 in ethanol is added dropwise to a solution of benzylamine in ethanol, heated under reflux overnight, and the solvent removed under vacuum. The residue is triturated with $CHCl_3$, filtered to remove benzylamine HCl, and distilled to remove any excess benzylamine. The product is dissolved again in $CHCl_3$ and filtered to remove the remaining benzylamine HCl. Evaporation of the solvent gives rise to a viscous oil, which is purified by vacuum distillation or column chromatography and characterized as 1-benzyl-2-ketopiperazine, 5.

(D) Hydrolysis of 5 with 6N HCl is achieved by refluxing for 40 hours, cooling, filtering, washing with a small amount of ice-cold water, and drying. The resultant residue is the dihydrochloride of N-(2-benzylaminoethyl)glycine, 6.

(E) A solution of 6 in 8N NaOH is added to a solution of BrCN in methanol with cooling and stirring. Stirring is continued after addition for 2 hours at room temperature. The product is filtered and crystallized from ethanol, or subjected to column chromatography to give 1-carboxymethyl-3-benzyl-2-iminoimidazolidine, 7.

(F) Deprotection of 7 is achieved either by reduction with sodium in liquid ammonia, or by reflux in HCl, giving rise to 1-carboxymethyl-2-iminoimidazolidine.

(G) 1-Carboxymethyl-2-iminoimidazolidine is treated with LiOH in an ice cold bath and reacted very cautiously with freshly distilled $POCl_3$. After 2 hours, the reaction is brought to reflux, acidified with 6N HCl, filtered, and washed with 30% methanol/water v/v. The washings and the filtrate are collected and evaporated in a vacuum. The solid residue is subjected crystallization to give 8 the dilithium salt of 1-carboxymethyl-3-phosphono-2-iminoimidazolidine dihydrate $C_5H_8N_3O_5PLi_2 \cdot 2H_2O$.

Alternatively, 6 can be deprotected to afford N-(carboxymethyl)ethylenediamine, which in turn is reacted with cyanogen bromide to yield cyclocreatine. See Scheme 5. CCr can then be phosphorylated by reaction with LiOH and $POCl_3$ as described.

Scheme 5

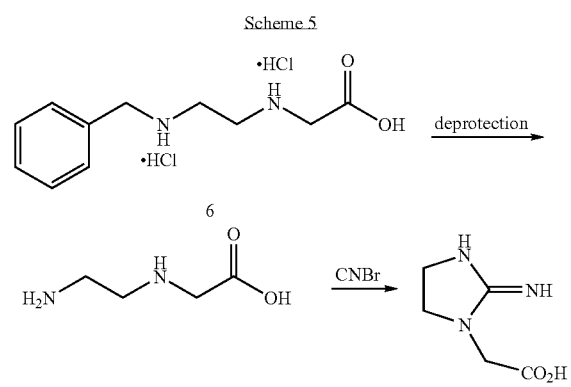

Cyclocreatine phosphate can be prepared from 2-iminoimidazolidine, 9, which can be prepared as described in Matsumoto, K., and Rapoport, H., *J. Org. Chem.* 33, 1968, 552-558, which is incorporated by reference in its entirety. See Scheme 6.

Scheme 6

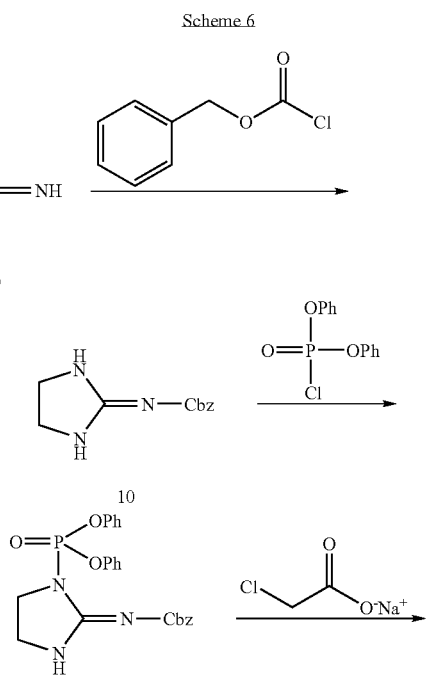

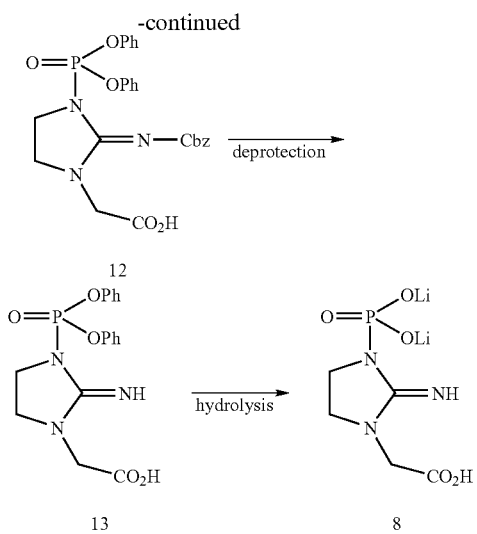

The imine nitrogen of 9 is protected with the carbobenzyloxy (Cbz) protecting group. One of the ring nitrogens can then be modified with a protected phosphoryl group, 11. The other nitrogen is modified with a carboxymethyl group, for example by reaction with sodium chloroacetate to form precursor 12 of cyclocreatine phosphate. 12 is then deprotected and hydrolyzed to afford cyclocreatine phosphate 8.

Variations of the methods above can be made. For example, other reagents, conditions, and protecting groups can be used to form the same compounds. Other phosphorylating agents (such as, for example, P(=O)(OPh)$_2$) can be used to add a phosphoryl group. Modifications to the compounds can also be made. For example, the imidazolidine ring of CCrP can be substituted with a hexahydropyrimidine ring; or the carboxymethyl group of CCr can be substituted with a carboxyethyl group.

1-carboxymethyl-3-phosphono-2-iminoimidazolidine (dilithium salt, dihydrate)

A solution of 0.5 g (3.5 mmol) of 1-carboxymethyl-2-iminoimidazolidine in 0.5 mL of 3.7 N lithium hydroxide and 5 mL water was cooled in an ice-salt bath. A freshly distilled portion of POCl$_3$ (1.6 mL, 17.5 mmol) in 32 mL of 3.7 N lithium hydroxide was added very cautiously portionwise (e.g., 16-20 portions) over a period of 2 hours, with mechanical stirring and cooling. After a further 2 hours, the pH of the solution was adjusted to 7.2 using 6 N HCl. Solids were removed by filtration or centrifugation and then washed with 30% methanol/water v/v. The filtrate or supernatant was combined with the washings, and subjected to vacuum at room temperature to reduce the volume to about 5 mL. The resulting slightly turbid solution was filtered through a fine-grade sintered glass funnel to give a clear filtrate. Absolute ethanol was added to the filtrate, which was then allowed to stand overnight. The resulting crystals were collected by filtration and recrystallized from water-ethanol. An additional crop was obtained by addition of ethanol to the mother liquor until it became turbid, allowing it to stand overnight, and filtering.

The methods described here can be used to produce CCr or CCrP on a large scale, such as kilogram quantities or greater. Large scale synthesis can be achieved in the following way.

A reactor is fitted with a cooling device to ensure efficient cooling between −20° C. and 0° C., preferably between −10° C. and −5° C. When the reaction is taking place, the temperature is maintained below 0° C.

The reactor also includes a technical thermometer, a dropping device, a stirrer, and a condenser.

The reactor also includes a technical thermometer capable of measuring temperatures between −10° C. and 5° C. The thermometer is configured to read the temperature of the reaction mixture. A dropping device (e.g., addition funnel, syringe pump, or the like) is configured to add reagents to the reaction mixture at a controlled rate, such as one drop per minute. The dropping device can be configured to include a drying agent (such as anhydrous calcium chloride) to remove any atmospheric moisture. The stirrer can be a mechanical or magnetic stirrer. The condenser can be connected to an exhaust.

A rigorously dry stoppered flask or bottle is used for the preparation of a solution of freshly distilled POCl$_3$ in LiOH. Transfer of the POCl$_3$ solution to the dropping device is performed carefully (e.g., in a closed system).

After complete addition of the POCl$_3$ solution to the CCr solution, the reaction mixture is stirred and cooled for an additional period of time, such as two hours.

Precooled 6N HCl is added to the reaction mixture portionwise. The temperature is maintained during the addition. The addition is continued until the pH reaches 7.2. The reaction mixture is then filtered (e.g., through a sintered glass filter) to remove solids. The solids are washed with 30% methanol/water (v/v) and collected. The volume of the combined filtrate and washings is reduced under vacuum, for example by rotary evaporator, to ~10% of the original volume. If the solution is turbid, it can be filtered again. Absolute methanol is added portionwise, with stirring, to the clear filtrate until slight turbidity is observed. The solution is allowed to stand overnight at room temperature. Crystals are collected and stored in a dry environment. Ethanol is added dropwise to the mother liquor until turbidity is observed. A further crystallization yields a second crop of the product.

Other embodiments are within the scope of the following claims.

What is claimed is:

1. A method of making a compound having the formula:

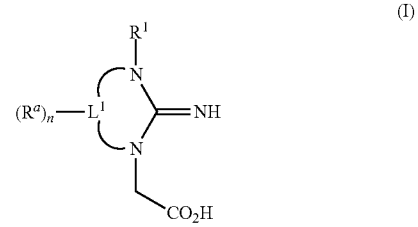

wherein L$^1$ is C$_1$-C$_4$ alkylene; R$^1$ is —H or —P(=O)(OH)$_2$; each R$^a$, independently, is hydrogen, alkyl, alkoxy, aryl, aralkyl, hydroxy, or halo; and n is 0, 1, 2, 3, or 4; or a pharmaceutically acceptable salt thereof, comprising:

contacting a compound having the formula:

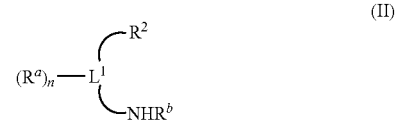

wherein L$^1$ is C$_1$-C$_4$ alkylene; each R$^a$, independently, is hydrogen, alkyl, alkoxy, aryl, aralkyl, hydroxy, or halo;

$R^2$ is hydroxy, alkoxy, or aryloxy; $R^b$ is hydrogen or alkyl; and n is 0, 1, 2, 3, or 4;

with a compound having the formula $L^2$-$CH_2$—CN, wherein $L^2$ is a leaving group, to form a compound having the formula:

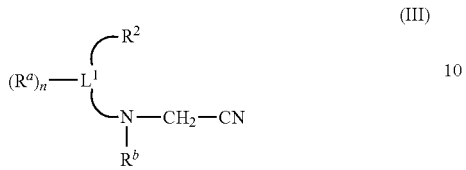
(III)

wherein $L^1$ is $C_1$-$C_4$ alkylene; each $R^a$, independently, is hydrogen, alkyl, alkoxy, aryl, aralkyl, hydroxy, or halo; $R^2$ is hydroxy, alkoxy, or aryloxy; $R^b$ is hydrogen or alkyl; and n is 0, 1, 2, 3, or 4;

converting compound (III) into a compound having the formula:

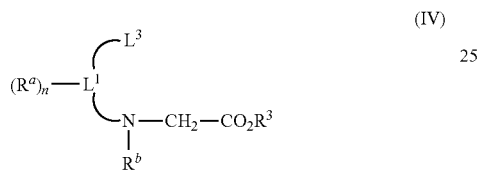
(IV)

wherein $L^1$ is $C_1$-$C_4$ alkylene; each $R^a$, independently, is hydrogen, alkyl, alkoxy, aryl, aralkyl, hydroxy, or halo; $R^b$ is hydrogen or alkyl; $L^3$ is a leaving group; and $R^3$ is hydrogen, alkyl or aryl; and n is 0, 1, 2, 3, or 4;

contacting compound (IV) with NH-$R^4$ to form a compound having the formula:

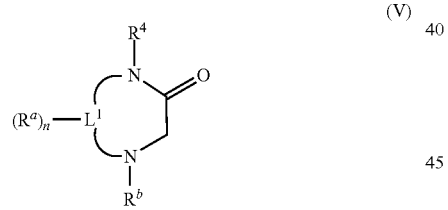
(V)

wherein $L^1$ is $C_1$-$C_4$ alkylene; each $R^a$, independently, is hydrogen, alkyl, alkoxy, aryl, aralkyl, hydroxy, or halo; $R^b$ is hydrogen or alkyl; $R^4$ is hydrogen, aralkyl or a protecting group; and n is 0, 1, 2, 3, or 4;

converting compound (V) into a compound having the formula:

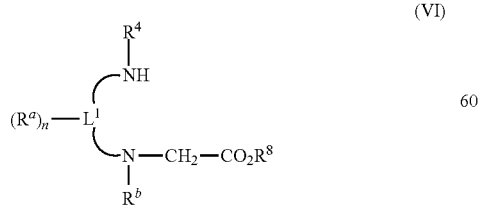
(VI)

wherein $L^1$ is $C_1$-$C_4$ alkylene; each $R^a$, independently, is hydrogen, alkyl, alkoxy, aryl, aralkyl, hydroxy, or halo;

$R^b$ is hydrogen or alkyl; $R^4$ is hydrogen, aralkyl or a protecting group; $R^8$ is hydrogen, alkyl, aryl, or a cation; and n is 0, 1, 2, 3, or 4;

contacting compound (VI) with cyanogen bromide to form a compound having the formula:

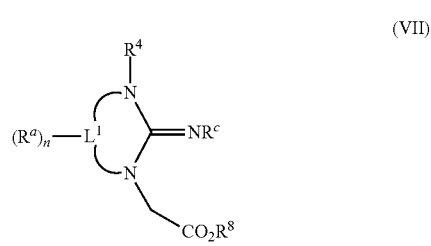
(VII)

wherein $L^1$ is $C_1$-$C_4$ alkylene; each $R^a$, independently, is hydrogen, alkyl, alkoxy, aryl, aralkyl, hydroxy, or halo; $R^b$ is hydrogen or alkyl; $R^4$ is hydrogen, aralkyl or a protecting group; $R^8$ is hydrogen, alkyl, aryl, or a cation; $R_c$, is hydrogen alkyl, aralkyl, or a protecting group; and n is 0, 1, 2, 3, or 4;

converting compound (VII) with into a compound having the formula:

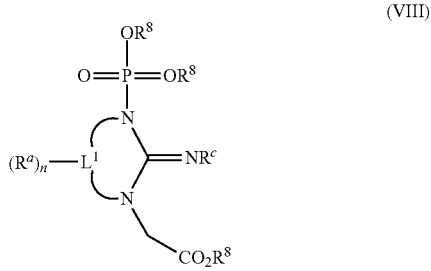
(VIII)

wherein $L^1$ is $C_1$-$C_4$ alkylene; each $R^a$, independently, is hydrogen, alkyl, alkoxy, aryl, aralkyl, hydroxy, or halo; $R^4$ is hydrogen, aralkyl or a protecting group; each $R^8$, independently, is hydrogen, alkyl, aryl, or a cation; $R^c$ is hydrogen, alkyl, aralkyl, or a protecting group; and n is 0, 1, 2, 3, or 4; or a pharmaceutically acceptable salt thereof.

2. The method of claim 1, wherein $L^1$ is $C_2$ alkylene, each $R^a$ is hydrogen, and $R^c$ is hydrogen.

3. The method of claim 1, further comprising converting the compound having the formula:

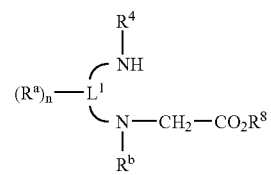

wherein $L^1$ is $C_1$-$C_4$ alkylene; each $R^a$, independently, is hydrogen, alkyl, alkoxy, aryl, aralkyl, hydroxy, or halo; $R^b$ is hydrogen or alkyl; $R^4$ is hydrogen, aralkyl or a protecting group; $R^8$ is hydrogen, alkyl, aryl, or a cation; and n is 0, 1, 2, 3, or 4;

into a compound having the formula:

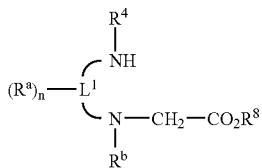

wherein $L^1$ is $C_1$-$C_4$ alkylene; each $R^a$, independently, is hydrogen, alkyl, alkoxy, aryl, aralkyl, hydroxy, or halo; $R^b$ is hydrogen or alkyl; $R^{4a}$ is hydrogen or —P(=O)(OH)$_2$; $R^8$ is hydrogen, alkyl, aryl, or a cation; and n is 0, 1, 2, 3, or 4; or a pharmaceutically acceptable salt thereof.

4. The method of claim 3, further comprising converting the compound having the formula:

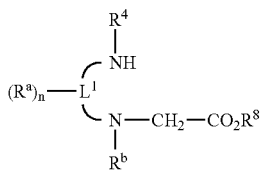

wherein $L^1$ is $C_1$-$C_4$ alkylene; each $R^a$, independently, is hydrogen, alkyl, alkoxy, aryl, aralkyl, hydroxy, or halo; $R^b$ is hydrogen or alkyl; $R^{4a}$ is hydrogen or —P(=O)(OH)$_2$; $R^8$ is hydrogen, alkyl, aryl, or a cation; and n is 0, 1, 2, 3 or 4 into a compound having the formula:

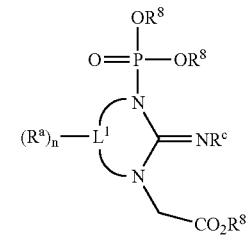

wherein $L^1$ is $C_1$-$C_4$ alkylene; each $R^a$, independently, is hydrogen, alkyl, alkoxy, aryl, aralkyl, hydroxy, or halo; $R^b$ is hydrogen or alkyl; $R^4$ is hydrogen, aralkyl or a protecting group; each $R^8$, independently, is hydrogen, alkyl, aryl, or a cation; $R^c$ is hydrogen, alkyl, aralkyl, or a protecting group; and n is 0, 1, 2, 3 or 4; or a pharmaceutically acceptable salt thereof.

5. The method of claim 4, wherein $L^1$ is $C_2$ alkylene, each $R^a$ is hydrogen, and $R^c$ is hydrogen.

6. A method of making a compound having the formula:

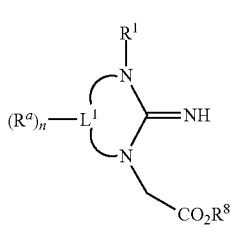

(IX)

wherein $L^1$ is $C_1$-$C_4$ alkylene; $R^1$ is —H or —P(=O)(OH)$_2$; each $R^a$, independently, is hydrogen, alkyl, alkoxy, aryl, aralkyl, hydroxy, or halo; $R^8$ is hydrogen, alkyl, aryl, or a cation; and n is 0, 1, 2, 3, or 4; or a pharmaceutically acceptable salt thereof, comprising forming a compound having the formula:

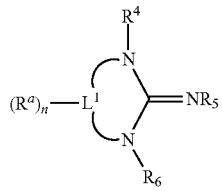

(X)

wherein $L^1$ is $C_1$-$C_4$ alkylene; each $R^a$, independently, is hydrogen, alkyl, alkoxy, aryl, aralkyl, hydroxy, or halo; and n is 0, 1, 2, 3, or 4; $R^4$ is hydrogen, aralkyl or a protecting group, $R^5$ is a protecting group; and $R^6$ is hydrogen, a protecting group, or has the formula —CH$_2$CO$_2$R$^8$, wherein $R^8$ is hydrogen, alkyl, aryl, or a cation, wherein forming the compound (X) includes protecting an imino nitrogen of 2-iminoimidazolidine;

converting the compound (X) into a compound having the formula:

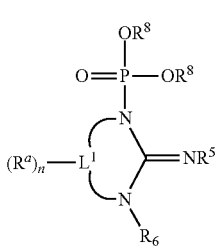

(XI)

wherein $L^1$ is $C_1$-$C_4$ alkylene; each $R^a$, independently, is hydrogen, alkyl alkoxy, aryl, aralkyl, hydroxy, or halo; and n is 0, 1, 2, 3, or 4; $R^4$ is hydrogen, aralkyl or a protecting group, $R^5$ is a protecting group; and $R^6$ is hydrogen, a protecting group, or has the formula —CH$_2$CO$_2$R$^8$ wherein $R^8$ is hydrogen alkyl aryl or a cation;

converting the compound (X) into a compound having the formula:

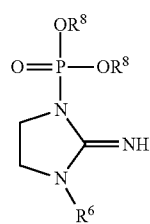

(XII)

wherein $R^6$ is hydrogen a protecting group or has the formula —CH$_2$CO$_2$R$^8$, wherein $R^8$ is hydrogen, alkyl, aryl, or a cation; and converting the compound (XII) into a compound having the formula:

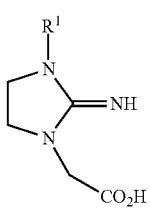

(XIII)

wherein $R^1$ is —H or —P(=O)(OH)$_2$, or a pharmaceutically acceptable salt thereof.

* * * * *